United States Patent [19]
della Valle et al.

[11] Patent Number: 5,457,034
[45] Date of Patent: Oct. 10, 1995

[54] VECTORS FOR EXPRESSION OF NGF IN EUKARYOTIC CELLS

[75] Inventors: Francesco della Valle; Lanfranco Callegaro; Alessandro Negro, all of Padua, Italy

[73] Assignee: Fidia, S.p.A., Italy

[21] Appl. No.: 156,792

[22] Filed: Nov. 24, 1993

Related U.S. Application Data

[63] Continuation of Ser. No. 614,004, Nov. 14, 1990, abandoned.

[30] Foreign Application Priority Data

Nov. 16, 1989 [IT] Italy ........................ 48564/89

[51] Int. Cl.$^6$ .................... C12P 21/06; C12N 15/00; C07K 13/00; C07H 17/00
[52] U.S. Cl. .................... 435/69.4; 435/69.8; 435/320.1; 530/399; 536/23.51
[58] Field of Search .................... 530/399; 435/69.1, 435/69.8, 69.4, 320.1; 536/23.1, 23.51

[56] References Cited

FOREIGN PATENT DOCUMENTS

| | | |
|---|---|---|
| 25252 | 7/1988 | Australia. |
| 30133 | 9/1989 | Australia. |
| 0121338 | 9/1989 | European Pat. Off.. |
| 0370171 | 5/1990 | European Pat. Off.. |
| 56741 | 11/1990 | WIPO. |

OTHER PUBLICATIONS

Scharf et al. 1986 Science 233:1076.
Sambrook et al 1989 Molecular Cloning: A Laboratory Manual CSHL Press, CSHL, N.Y. pp. 16.17–16.26.
Meier et al. 1986. Mol. clon. of bovine & chick NGF: delineation of cons. & uncons. domains & relationship to bio. act. . . . EMBOJ5:1489.
Selby et al 1987 Mouse NGF gene: Structure and Expression Mol. Cell. Biol. 7(9):3057–3064.
Ullrich et al 1983. Human β–NGF gene sequence highly homologous to that of mouse. Nature 303:321.
Scott et al. 1983. Isolation and nucleotide seq. of cDNA encoding The precursor of m. NGF. Nature 302:538.
Edwards et al. 1988. Processing & Secretion of NGF: Expr. in Mammalian Cells w/Vaccinia Virus Vector Mol. Cell. Biol 8(6):2456.
G. Zettlmeissl et al Biotechnology, vol. 5, No. 7 (Jul. 1987) pp. 720–725.
N. Israel et al Gene, vol. 51, No. 2–3 (1987) pp. 197–204.
Barinaga 1994 Science 264:772–774.
M. Iwane et al., Biochem. Biophys. Res. Comm. 171:116 (1990).

Primary Examiner—Garnette D. Draper
Assistant Examiner—K. Cochrane Carlson
Attorney, Agent, or Firm—Birch, Stewart, Kolasch, & Birch

[57] ABSTRACT

This invention relates to a process for obtaining, from transformed cells, the polypeptide called nerve growth factor (β-NGF), and more precisely to the process for obtaining, by recombinant DNA technology using genetic constructions insertible in appropriate eukaryotic cell lines, the biologically active human mature form (β-subunit).

4 Claims, 8 Drawing Sheets

VECTORS FOR EXPRESSION OF NGF IN EUKARYOTIC CELLS

This application is a continuation of application Ser. No. 07/614,004 filed on Nov. 14, 1990, now abandoned.

FIELD OF THE INVENTION

This invention relates to a process for obtaining, from transformed cells, the polypeptide called nerve growth factor (β-NGF), and more precisely to the process for obtaining, by recombinant DNA technology using genetic constructions insertible in appropriate eukaryotic cell lines, the biologically active human mature form (β-subunit).

BACKGROUND OF THE INVENTION

A. Nerve Growth Factor (NGF)

The nerve growth factor (NGF) was first discovered in mouse sarcoma tumors (Levi-Montalcini, R. et al., J. Exp. Zool. 116:321, 1951) and was then purified and brought to homogeneity from male mouse salivary submaxillary glands (Varon, S. et al., Biochemistry 6:2202, 1967) and from snake venom (Angeletti, R. H., Proc. Natl. Acad. Sci. USA 65:668, 1970). Many other relatively rich NGF sources have been indicated, including guinea pig prostate (Harper, G. P. et al., Nature 279:160, 1979) and human placenta (Goldstein, L. D. et al., Neurochem. Res. 3:175, 1978, Walker, P. et al., Life Science 26:195, 1980, Fidia Patent 47745A88). Small amounts of NGF have been found in other tissues such as, for example, the mammal central nervous system (Whittemore, Scott, R. et al., Brain Research 12, 439–464, 1987. The physiological relation between these potential sources of NGF and the apparent action sites is not very clear but generally it is supposed that NGF is secreted by various peripheral tissues that require innervation from those cells that respond to the NGF.

The NGF obtained from the mouse submaxilliary glands is the one mostly used for studies of the activity of NGF in vitro and in vivo. The range of biological activity in vitro of NGF was determined both on primary nerve cells and on cloned cell lines. Of the primary nerve cells that responded to the NGF in vitro are fetal sensory neurons (fetal day 8–12) from the spinal ganglion roots, autonomic noradrenergic fetal neurons from the sympathetic ganglion, cholinergic fetal neurons from the septum and chromaffin suprarenal cells during development. While the sensory and sympathetic neurons depend on NGF to survive and develop, the cholinergic neurons do not seem to need NGF for survival but only for their differentiation, i.e., for expression of the phenotypic characteristics linked to the neurotransmitter. The addition of NGF to the chromaffin suprarenal cells (derived from the neural crest) during the first phase of their development causes the expression of nerve phenotypes. Of the cells lines that respond to the NGF in vitro, as described in the literature, included are the chromaffin suprarenal cells derived from tumors of the neural crest, called pheochromocytoma cells (PC12) and human neuroblastoma cells. After treatment with β-NGF, these cells change their behavior, going from a strongly proliferative phase to a postmitotic condition.

The nerve growth factor obtained from mouse submaxillary gland is the one which is most characterized, also with a chemical and immunochemical profile. The NGF from murine glands acts like a protein complex of the 7S type (molecular weight about 140,000 daltons) made up of three subunits (α, β, γ) that coordinate a $Zn^+$ atom.

The most interesting part of the 7S molecule, relative to biological activity, is constituted by two polypeptide chains, each having a molecular weight of 13,250 and formed by 118 amino acids. Each chain or monomer has three sulfide bridges, that form covalent bonds between two cysteine residues, which confer a strong stability to the tridimensional structure of the protein. The two monomers of NGF joined to one another by weak bonds form a dimer with molecular weight of 26,500. It has been shown that the biological activity is associated with the dimer called 2.5S or conventionally β-subunit. It is not known if this is present also in the monomer.

The techniques of genetic engineering have made it possible to identify the gene that codes for the β-subunit of NGF (β-NGF) (Scott, J. et al., Nature 302:538, 1983; Ullrich, A. et al., Nature 303:821, 1983; EP Patent Publn. No. 0 121 338). The human gene that codes the molecule is located in the short arm of chromosome I and codes for the synthesis of a molecule much larger than that of molecular weight of 26,500 that constitutes the biologically active molecule. Therefore, the gene initially instructs the synthesis of a NGF precursor or pro-NGF of greater dimensions. It has further been demonstrated that the gene coding for the β-subunit of NGF is highly conserved in different species, from birds to man (Meier, R. et al., EMBO J. 5:1489, 1986).

The elucidation of the nucleotide sequences of murine, human, bovine and chick β-NGF has made possible a comparison between the conserved sites and those not conserved of these molecules and their relationship to biological activity and antigenicity. The overall conservation of β-NGF during the evolution is surprisingly high. Of 118 amino acids of the mature form of NGF purified from male mouse salivary submaxillary glands, only 16 amino acids are different in bovine β-NGF, 19 in chick β-NGF and 11 in human β-NGF, while there are only 6 amino acids of difference between bovine and human β-NGF. All the cysteine residues are rigorously conserved in all species. The reduction of the three S-S bridges of β-NGF causes the complete loss of its biological activity. The apparent discrepancy between the high level of overall conservation of amino acid sequences and the low cross-reactivity of the immunochemical type is due to the fact that the changes of the amino acids between species are located in specific "clusters." With hydropathic tracings it is possible to demonstrate that these changes occur almost completely in hydrophilic sites considered as potential antigenic determinants. Only one hydrophilic region was seen to be strictly conserved in the NGF molecules for all species studied so far.

B. Recombinant DNA Technology

Recombinant DNA technology makes it possible to construct vector series that are able to express proteins of interest in large amounts. This technology enables molecular biologists to assemble DNA sequences to create hybrid molecules capable of producing a protein of interest. The methods use various reactions such as cutting with restriction enzymes, joining of fragments thus obtained with ligase, chemical synthesis of oligonucleotides to be assembled and other available methodologies of various laboratories in the sector (Mariatis, T. et al., Molecular Cloning. A Laboratory Manual. Cold Spring Harbor Laboratory, Cold Spring Laboratory N.Y., 1982). To obtain high levels of expression, the DNA elements to be assembled must present essential information. For example, a replication origin, a selection for antibiotics, an expression promoter, activators of the transcription of the gene of interest and other characteristics known to cultivators of said material. The combination of these elements in a suitable way gives rise to a vector, if the gene of interest is inserted naturally with respect to the regulatory sequences of the transcription and translation and the resulting plasmid is defined in expression. The plasmid or expression vector is thus able to express the protein in host cells. The protein then can be obtained by a purification system. The elements (promoters) that naturally control the expression of many genes, such as, for example, growth factors, are not very strong in their expression and are activated only in natural suitable conditions that often are not known. For this purpose, promoters are used whose activity is known, for example the virus of the papovavirus series, or other known promoting gene sequences. The elements that are used for high levels of expression therefore are a combination of DNA of various origin (eukaryotic, bacterial, viral, etc.) constituted at the end of different gene portions joined to form a hybrid. The transcription and translation activity of a gene depends on the suitable distances between regulatory and coding sequences.

With this introduction being given, one of the best modes for suitable working of the regulatory sequences is that where the introduced gene is placed in the identical position as in the natural gene. One system that is used is that in which the regulatory sequences comprise also some nucleic acids of the coding sequences. Union with the introduced gene then results in a fused protein. If, on the other hand, the fused portion is removed, it is possible to obtain higher biological values. If the technique of fusion proteins is not used, the conventional technologies for obtaining genes located in close vicinity of the regulatory sequences depend on the existence of suitable restriction sites that permit their cloning. If compatible sites do not exist in the vicinities but at different sites, it is possible to obtain union of the segments with the synthesis of an oligonucleotide or linker that contains the desired restriction site. If restriction sites to permit the use of the linker do not exist in the vicinity, then the technique of deletion of the DNA with Bal 31 or S1 is used. This possibility does not allow a precise deletion and it is always necessary to check by sequencing the various clones to see which is the most suitable. These systems are very limiting for the molecular biologist and consequently it is necessary to develop alternative strategies as a function of the advent of new technologies, such as that of polymerase chain reaction (PCR) (Saiki et al., Science 239:487, 1988; Scharf, S. J., Science 233:1076, 1986).

With this technique it is possible to amplify a gene segment up to $10^6$. The principle is based on the use of two oligonucleotides that can be paired, respectively each on one of the DNA strands to be amplified. The distance that intervenes between two oligonucleotides with respect to the examined gene sequence gives the dimensions of the molecule to be produced. These two oligonucleotides are constructed so that inside their sequence there is a restriction site that allows their subsequent cloning. This restriction site is present naturally or is constructed ad hoc by degenerating the minimum number of bases. This approach, which can be defined as site-directed mutagenesis, makes it possible to construct restriction sites in positions theoretically determined by the molecular biologist. The construction of sites compatible with other gene segments permits, on the one hand, easy cloning but especially opens up the possibility of uniting various gene segments in an aimed way. This technique can be defined as cloning by direct mutagenesis. In practice, by recombinant DNA technology, it is possible to express complete heterologous polypepides by direct expression, or alternatively the heterologous polypeptide fused with an amino acid sequence portion of a similar polypeptide can be expressed. In general, products obtained in this way are not biologically active (British Patent Application Publ. No. 2007676A; Wenzel, American Scientist 68, 664, 1980).

The capability of isolating the human gene of the β-subunit of the nerve growth factor offers us an important possibility. It is possible by recombinant DNA technology to produce a sufficient amount of this rare protein. Actually, the nerve growth protein can be accepted for clinical use in the treatment of various neurodegenerative diseases. In this sense there is documentation relative to obtaining the β-subunit of NGF by recombinant DNA technology (European Patent Publ. No. 0121388; Bruce, G. et al., Neurobiology of Aging 10:89, 1989; Hu, G. et al., Neurobiol, Aging 70:57, 1988; Edwards, R. H., Mol. Cell. Biol. 8:2456, 1988; Emfors, P., Proc. Natl. Acad. Sci. 86:4756, 1989). For the production, mammal cells are selected rather than bacteria only in those cases where less expensive expression in microbial cells is not feasible. Actually, it is much more economical to produce certain proteins in bacterial lines such as *E. coli,* but generally this host/vector system faithfully reproduces only the linear sequence of the amino acids that make up the protein, obtaining a kind of insoluble mass in the bacterium. Assuming that a given product can be prepared from this material in an economically advantageous way, *E. coli* could be the system of choice, as in the case of certain smaller molecules, such as interferons and some animal growth proteins where a correct folding of the molecule in vitro is feasible. These systems are most productive in cases that generally relate to those proteins with a single disulfide bond and with peptides or protein whose use (as diagnostic antigens or vaccine components) does not require a well-defined conformation.

Therapeutic proteins, to which the nerve growth factor (β-NGF) belongs, require a correct conformation to be active and usable and also need to be free of antigenic response. The preparation process could comprise, for the protein obtained from recombinant DNA, glycosylation, the formation of correct disulfide bonds and other post-translation modifications. The bacterial line *E. coli* is not able to meet this requirement, while mammal eukaryotic cells and yeasts are able. The potential application of human β-NGF as a pharmaceutical agent, obtained by biotechnology, should take these problems into consideration.

The activity of the NGF has been shown to depend on the dimeric form, i.e., the assembly of two similar polypeptides of 118 amino acids. Reduction with mercaptoethanol makes the biological activity drop practically to zero. Attempts at renaturation of three disulfide bridges make reassembly of the cysteine give rise, from the statistical viewpoint, to a molecule with correct structure and equal to that corresponding to the natural one with a probability of 1 out of 15. Consequently obtaining the molecule in *E. coli* does not guarantee the homology of the structure and its application as a pharmaceutical agent in man. Actually, after being purified to homogeneity, the human NGF produced from *E. coli* shows in immunoblotting, by polyclonal antibodies specific for the murine β-NGF, a series of bands that are not attributable to the biologically active dimeric form. Further, the biological activity of this mixture of structures and forms has been shown to be 10 times less as compared to the similar human form purified from natural sources, such as placenta tissue.

This approach of cloning and obtaining the nerve growth factor in *E. coli*, if on the one hand it produces high expression levels of the protein of interest, produces a series of inexact molecules which administered in vivo could cause secondary effects, for example, antibodies that would recognize and block the biological activity of the molecule present naturally. At the same time, cloning of the mature molecule in *E. coli* exhibits an irremovable initial methionine that is certainly immunogenic, because it is placed in an exposed part of the molecule.

Another approach relates to cloning the prepro NGF in eukaryotic cells and consists of taking advantage of the attack of the specific peptidases present naturally in the eukaryotic cells to obtain the mature molecule. In particular, cloning is performed on cells of Chinese hamster ovary (CHO). From current literature, entire genomic cloning of the human NGF has not yet been sequenced but it has been shown that the gene is extended for more than 10 kda (Ullrich, A. et al., Nature 303:821, 1983). The gene thus extended does not permit conventional cloning, going from this entire genomic sequence. The approach is that of cloning a portion of the cDNA that contains only the coding portions of the protein. At the moment, the complete cDNA for human NGF has not yet been isolated (some sequences are lacking at the 5' position) but much information is known of the NGF messengers of other origin (mouse, bovine, chick, etc.) (Meier, R. et al., EMBO J. 51489, 1986; Selby, H. J., J of Neuron Research 18:293, 1987) that can lead to interesting deductions. The mouse NGF gene is present in single copy and produces at least four different messengers of different dimensions (Meier R. et al., EMBO J. 5:1489, 1986; Selby, M. J., J. Neurosci. Res. 18:293, 1987). These different dimensions are reflected especially in the different starting AUG codon, the most important are at positions −187 and −121 with respect to the mature protein. These messengers are present in different relative abundance with respect to various tissues. Those that begin at −187 are 10 times more abundant in the submaxillary gland in comparison with those that begin at −121. However, different evidences have shown that the most consistent percentage of the NFG messengers expressed in the brain use precisely the AUG at −121.

SUMMARY OF THE INVENTION

The present invention, therefore, relates to a process for obtaining the β-subunit of the human NGF by expression vectors, so that a natural distance exists between the regulatory sites and those coding said protein, vectors to be used on eukaryotic cell lines, for example CHO, which make it possible to obtain on culture medium the mature form of the β-subunit of the human nerve growth factor (hβ-NGF), in the absence of one or more amino acids fused to the polypeptide, different from those present in its natural sequence. The polypeptide thus obtained shows biological activity used on suitable target cells.

The hβ-NGF described in this invention can be used for maintenance or prevention of loss of the nerve function, for its recovery in pathological conditions of the chronic or acute type, in neurodegenerative situations even in tardive phases of acute pathologies, such as cerebrovascular, infective, inflammatory, compressive, metabolic deficiencies and in situations of modulation of the immune system. The polypeptide obtained is further without other contaminating proteins of human origin that could exhibit undesirable biological activity.

The invention is further directed at genetic constructions that can be used for cell transfections, including those that can be implanted in vivo. Some of these constructions can produce, at the local level, specifically the active form of the human growth factor as a function of a diet administered, i.e., it is possible to keep the gene under control.

The invention is further directed at the transformed cell line, which contains said vectors, and to its culture that produce the hβ-NGF. The object of this invention is also the pharmaceutical preparations comprising as active substances one or more new complexes of β-unit of the neurotrophic factor and a natural ganglioside or one of its derivatives or semisynthetic analogs or one of its salts.

DETAILED DESCRIPTION OF THE INVENTION

Figure 1:
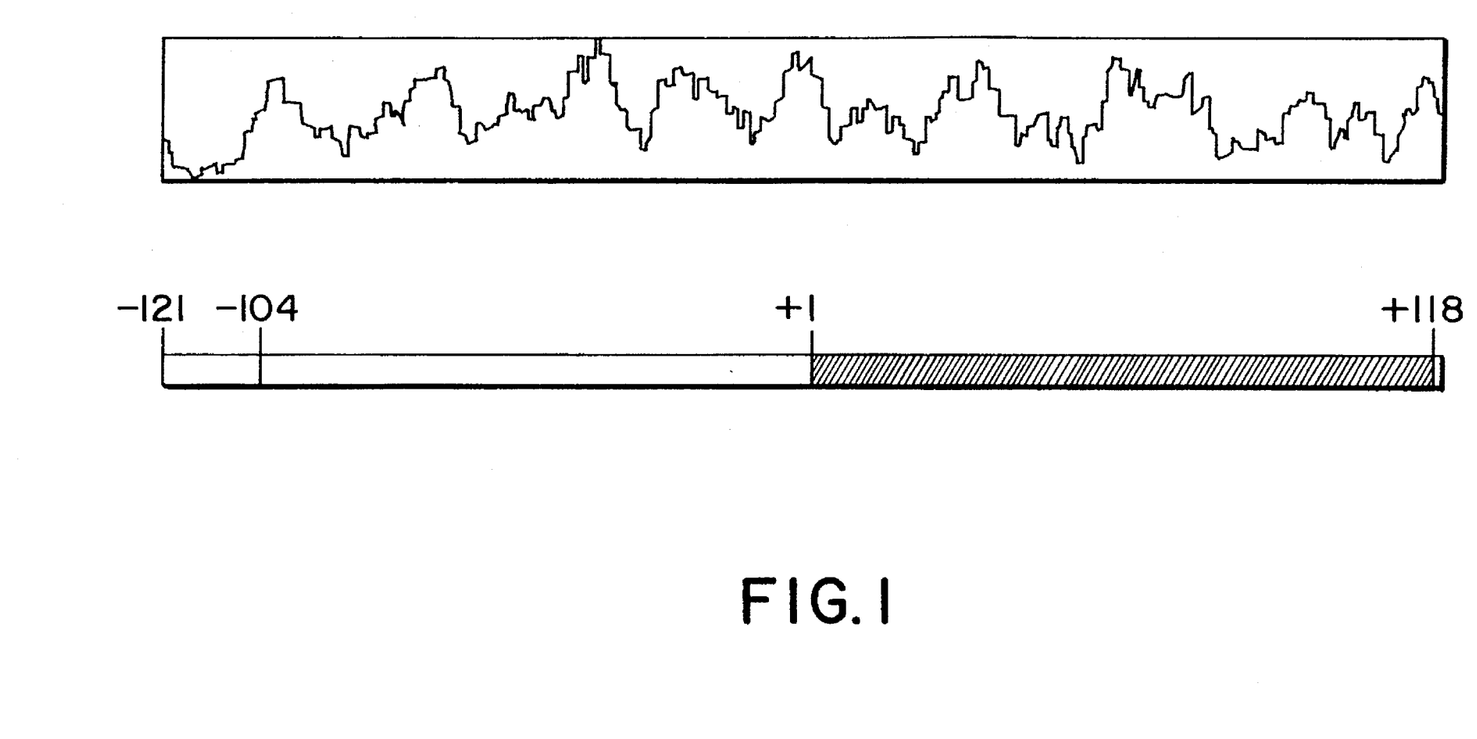
FIG. 1 is an hydropathicity profile of the polypeptide of the nerve growth factor, β-subunit, of human origin.

Starting from these evidences, the human β-NGF of the present invention was cloned, starting precisely from methionine at −121. Analyses of the hydropathicity profile showed that amino acids between −121 and −104 can function as leader peptide, indicating that the protein can be secreted. This profile is shown in FIG. 1, the hydropathicity profile of the polypeptide of the nerve growth factor, subunit, of human origin, according to the method described (Hopp et al., Proc. Natl. Acad. Sci. USA 78:3824, 1981). The position indicated as −121/−104 identifies the leader peptide while the position indicated as +1/+118 indicates the amino acid sequence of the polypeptide of the nerve growth factor, β-subunit, of human origin (Ullrich et al., Nature 303:821, 1983). To obtain the mature protein there exists a specific peptidase that makes it possible to obtain the amino acid sequence from +1 and at +118 that corresponds to the biologically active peptide. This peptidase contained in the cells that normally synthesize NGF was shown to be contained also in the AT-20 cells. Actually, by introducing into these cells a vector consisting of a Vaccinia Virus prepro NGF of murine origin, they are able to secrete mature NGF making possible the production of a molecule of 14 kda in gel under denaturing and reducing conditions (Edwards, R. H., Mol. Cell. Biol. 8:2456, 1988).

As a function of the preceding experiences in obtaining the β-subunit of the nerve growth factor, described above, the present inventors compared in an innovative way the construction of one or more vectors that can be used in eukaryotic cells. PCR technique was used to perform the cloning of the prepro NGF, with which sites were created compatible with various expression vectors, and these restriction sites were located so as to maintain as natural as possible the distances between the regulatory sequences and coding sequences, a situation quite different from the genetic constructions previously described in literature for the expression of the β-NGF subunit. The portion of the prepro NGF was joined to a modified mature human NGF (hβ-NGF) sequence, acquired from British Technology Ltd. (Oxford, Great Britain), in which restriction sites are created to permit the subsequent mutagenesis. For the purpose of the invention, the presence of these restriction sites should not be considered limiting, just as the origin of the gene should not be considered limiting.

Starting from this assumption, the present inventors then cloned the prepro hβ-NGF under the control of different promoters SV40 (Simian Virus 40), MMTV (Mouse Mammary Tumor Virus), hMTIIa (human metallothionein IIa). These genetic sequences introduced into the plasmids were then transfected in CHO cells, showing that even these cells are able to produce in the culture medium the h-NGF polypeptide in its biologically active form. This prepro NGF has proved essential in the assembly of the molecule, making possible the expression of only the β-subunit and showing that the entire genetic construction was to be considered correct.

A. General Methods Employed:

The attacks on DNA chains with restriction enzymes are performed according to the specifications of producing companies. In general 1 μg of the plasmid is cut with 1 U of enzyme in 20 μl of solution; the temperature and incubation time depend on the enzyme used, in general 1 hour at 37° C. After incubation, the plasmid and genetic segments are purified in an agarose gel LMP Agarose (BRL, United States of America) in 40 mM of tris/HCl, 20 mM of sodium acetate, 1 mM of EDTA and then eluted from the agarose with the kit GENECLEAN™ (BIO 101 Inc., La Jolla, Calif., USA). For the copying reactions at the 5' end, the DNA is treated for 15 minutes at 15° C. with 10 U of polymerase (Klenow). For the ligases, ligase T4 is used in a concentration of 1 U per 0.5 μg of DNA in a reaction of 20 μg at 13° C. for 12 hours.

Analyses to confirm the correct sequences in the plasmid are performed by transforming in HB101 cells and the selected transformants in agarose plates in LB (Luria Bertani) medium with ampicillin antibiotic 50 μg/ml. The plasmid contained in the HB101 is grown in LB, 100 μg/ml of ampicillin and purified, either for small or large preparations with the kit of Quiagen (DIAGEN GmbH, Duesseldorf, Federal Republic of Germany). The expression vectors are prepared from bacterial cells with the Quiagen method.

The DNA for PCR reactions is prepared in the following way from human placenta at term. A piece 0.4 cm³ of chorionic villi is chopped up with a pair of scissors and suspended in 700 μl of 50 mM of tris/HCl pH 7.8, 100 mM of EDTA, 100 mM of NaCl, 1% of SDS. To this is then added 35 μl of proteinase (K 100 μg/ml) and incubated overnight at 55° C. Then 20 μl of a solution is added to 13 μg/ml of RNAase A and incubated for another 2 hours. Two extractions are made with phenol and two with chloroform. The DNA is then made to precipitate on a glass capillary by addition of 1 volume of isopropanol. At this point some passages are performed with 70% and 100% ethanol and drying is performed. The DNA is dissolved in a buffer (10 mM of tris/HCl pH 7.4, 1 mM of EDTA), leaving it in slow agitation in a test tube. After some hours, the dissolved DNA is ready for genetic amplification. Normally, 0.1 μg of DNA is sufficient to proceed to PCR.

Transfection on the CHO cells (CCL 61) and CHO modified by the absence of dehydrofolated reductase gene (DHFR-) are performed with liposomes by following the procedures of the producing company GIBCO or with calcium phosphate.

A.2 Transfection of Liposomes

The cells grown in alpha-MEM with 5% bovine fetal serum, the day before transfection are trypsinized and replated so that the next day they would reach 70–80% of the confluence. The plasmid DNA to be transfected is diluted to a concentration of 10 μg of DNA in 50 μl of $H_2O$ to which is then added 50 μl of Lipofectin™ (GIBCO), the whole in a polystyrene tube. After 15 minutes waiting, this mixture is added to the cells previously washed with the medium OPTI-MEM (GIBCO). The cells are incubated in this way for 8 hours, and then the normal medium including fetal bovine serum was added to continue the growth.

A.3 Method of Transfection With Calcium Phosphate to Obtain Stable Transformation The buffers for the transfection in this method are: BBS concentrated twice (2×BBS) and 0.25M of $CaCl_2$. The 2×BBS is prepared as follows: 50 mM of N,N-bis-2-(hydroxyethyl)- 2-amino ethane sulfonic acid (Calbiochem); 280 mM of NaCl and 1.5 mM of $Na_2HPO_4$ are dissolved in water and the pH is brought to 6.5, and then the whole is filtered at 0.45 μm, while the 10×$CaC_2$ is prepared as solution of 2.5M of $CaCl_2$.

The cells are sown $5 \times 10^5$ cell/10 cm plate/10 ml of growth medium and incubated at 35° C. overnight. 20 μg of plasmid is mixed with 0.5 μl of 0.25M of $CaCl_2$ and 0.5 ml of 2×BBS; the mixture is incubated for 15 minutes at ambient temperature. The mixture is then instilled in the medium and the whole was incubated overnight at 35° C. in 3% of $CO_2$. To obtain stably transformed cells with our vectors, a cotransfection is performed by adding to the vector expressing hβ-NGF the pSV2Neo vector in a ratio of 10 to 1. Two days after the transfection, the cells are trypsinized and sown in plates in a concentration ten times less in comparison with the transfection and immediately the selection is begun of the stable transformations with 1 mg/ml of G418 neomycin sulfate (Gibco). The transformants are then analyzed in Southern blotting for integration of the genetic construction.

A.4 Expression

All the media of the cells are kept for expression in Ham's F12/DME H-21 with 15 mM of Hepes and 10% of fetal calf serum. The medium is changed every three days and substituted with fresh medium without serum for purification of the hβ-NGF.

B. Preferred Embodiments

B.1. Description of the construction of Expression Vectors

Three different vectors are made; the first and second are two vectors in which the regulatory elements, respectively MMTV (Mouse Mammary Tumor Virus) and hMTIIA (human metallothionein IIa), can be chemically induced. In this way it is possible to controllably express the hβ-NGF gene. On the contrary, in the third vector, the hβ-NGF is cloned under the promoter SV40 (Simian Virus 40).

B.2. Cloning in the pMSG Expression vector

The pMSG vector was acquired from Pharmacia (Uppsala, Sweden). In accordance with the specifications of the company, the gene to be introduced must be inserted in multiple cloning sites between the Nhe I and Sal I restriction sites. The gene is translated by its first AUG; in this case the nerve growth factor is under the control of the promoter of the MMTVLTR (Mouse Mammary Tumor Virus Long Terminal Repeat). The activity of this promoter can be induced by administration of glucocorticoids, for example, dexamethasone. In the transcription, splicing takes place by means of the SV40 small t-antigen and polyadenylate by means of SV40 large t-antigen. This plasmid also contains the bacterial gene of the xanthine guanine phosphoribosyltransferase (xgpt) that is used to select the stably transformed CHO KI cells.

To permit a cloning in this plasmid of the prepro NGF, the PCR technique is used, with which a restriction site is created just before the initial AUG so as to keep the distances between the regulatory sequences and the coding sequences of the prepro NGF as natural as possible. Two oligonucleotides are synthesized: the first, between the bases 9122 and 9147 (Ullrich, A., Nature 303:821, 1983), should have the following sequence (SEQ ID NO:1):

---
5'GCATAGCGTA ATG TCC ATG TTG TTC T$_3$
Met Ser Met Leu Phe
---

The bases before the initial AUG, as noted above, are mutated and then the synthesized oligo has the following sequence (SEQ ID NO:2):

---
XbaI
5'TGT CTAG AGT ATG TCC ATG TTG TTC T$_3$
Met Ser Met Leu Phe
---

This oligonucleotide is called (XbaI). The second oligonucleotide, which comprises the bases between 9521 and 9342 (Ullrich, A., Nature 303:821, 1983), is complementary to this sequence to permit PCR and has the following sequence (SEQ ID NO:3):

---
EcoRI
5'GGCGG AATT CTCGGTGGTGGAC$_3$
---

This oligonucleotide contains on its inside the EcoRI site to be able to permit the joining of the prepro NGF to the mature NGF. This oligonucleotide was called (ECORI).

The two oligonucleotides are synthesized on an oligonucleotide synthesizer in solid phase with the method of phosphoramidites by following the standard procedures of a 330B DNA Synthesizer (Applied Biosystems, USA). They are: (a) treated a 55° C. for 12 hours in NH$_3$; (b) brought to dryness in a vacuum centrifuge; (c) resuspended in ammonium acetate 2.5M; (d) precipitated with 3 volumes of cold ethanol (−20° C.); and (e) rewashed with 80% cold ethanol and resuspended in water. The concentration of the two oligonucleotides are evaluated with a spectrophotometer. The amplification procedure is performed on a Perkin Elmer Cetus DNA Termal Cycler Amplificator and the reagents used for the amplification are those of the related kit DNA™ Amplefyor (Perki Elmer-Cetus). There is briefly used a mixture with 200 μM of each oligonucleotide, 0.5 μM of each dATP, dTTP, dCTP, dGTP oligonucleotide and 0.1 μg of human DNA and reaction buffer in a total mixture of 100 μl with 0.5 U of TAQ polymerase, the whole covered with paraffin oil to prevent evaporation. The amplification reaction is performed by operating the instrument for 35 cycles in the case of human DNA. The cycle in both cases is the following: 1 minute at 94° C., 2 minutes at 45° C., 3 minutes at 72° C. The amplified fragment of 300 bp was purified in a Low Melting Agarose (NuSieve) gel by using the GENECLEAN™ kit (BIO 101 Inc., La Jolla, Calif., USA) to dissolve the agarose. The DNA is cut with XbaI and EcoRI restriction enzymes and repurified as above. The fragment thus purified is cloned in the XbaI and EcoRI sites of the pGEM4 vector (Promega). The plasmid obtained is called pGEM4Xba-NGF.

This plasmid (pGEM4Xba-NGF) is cut at HindIII-EcoRI and the fragment of 300 bp, when purified, is cloned in HindIII-EcoRI sites of the pUC18BBG26 vector (British Biotechnology Ltd. Oxford, UK). The pUC18BBG26 contains the gene of the cassette-constructed hβ-NGF, i.e., inside its sequence are created restriction sites that are not natural that therefore make possible the substitution of determined domains, i.e., in other words, they permit mutagenesis. The vector obtained is called pUC18hNGFC. This vector is cut with BamHI and the extension copied at 5' with Klenow polymerase. It is cut at XbaI and the fragment of 760 bp is purified by an agarose gel. This fragment is cloned between the NheI and SmaI sites of the pMSG expression vector. The summary diagram for obtaining this vector, called pMSGphNGF, is set forth in FIG. 2, while the diagrammatic representation of the same vector is indicated in FIG. 3.

B.3. Cloning of NGF Under the Control of Metallothionein

This vector is made because metallothionein IIa (MTIIa) can be induced with Zn$^{++}$ or with Cd$^{++}$ or with other heavy metal ions, therefore its expression can be controlled. Further, to potentiate the expression of this promoter, SV40 enhancer is added at the 5' end of the promoter of the MTIIa, while the small t-antigen and the polyA of the SV40 are always used for splicing and polyadenylation. First the promoter of the metallothionein is joined to the prepro hβ-NGF as follows: the promoter of the metallothionein is isolated from the plasmid (phMTIIA) by cutting with restriction enzymes HindIII and BamHI (Karin, H., Nature 299:797, 1982), the fragment of 841 bp comprising the promoter is cloned in the sites HindIII-BamHI of the pGEM4 vector (Promega Madison, Wis., USA). This vector is called pGEM4hMTIIa. This promoter portion extends to 3' with some natural codons, contains the first codon of the AUG methionine and immediately after there is found the BamHI restriction site. To permit cloning of the prepro hβ-NGF under this promoter by using the initial methionine of the promoter of the hMTIIa, an oligonucleotide is constructed between the bases 9133 and 9160 (Ullrich, A., Nature 303:821, 1983) creating a BamHI restriction site just after initial AUG which would permit bringing the gene into phase. The synthesized oligonucleotide having the following sequence (SEQ ID NO:4):

```
5'TG TCC ATG TTG TTC TAC ACT CTG ATC AC3
   Met Ser Met Leu Phe Tyr Thr Leu Ile
``` is mutated into the following sequence (SEQ ID NO:5):

```
                    BamHI
       5'TGG ATCC ATTGTTCTACACTCTGATCAC3
```

This oligonucleotide is called BamHI. The changed bases comprise a change also of the amino acid sequence; actually, the 2nd and 3rd amino acids change, respectively, from Ser to Asp and from Met to Pro. However, this change does not have much influence on the hydropathicity profile and the molecule is secreted normally.

This oligonucleotide, together with the EcoRI oligonucleotide, is used to amplify the prepro NGF as above. The purified fragment is cut at BamHI and EcoRI and then cloned between the BamHI and EcoRI restriction sites of the pGEM4hMTIIa vector. The vector is called pGhMTphNGF.

To obtain the enhancer (activator) of SV40, the latter is taken from the PMSGphNGF plasmid as follows: the PMSGphNGF vector is cut BamHI and then the extension copied at 5' with Klenow polymerase. Then it is cut with HindIII and the fragment of 500 bp is cloned in pGEM3 between NaeI and HindIII restriction sites. The vector obtained was called pGSV40.

Figure 4:
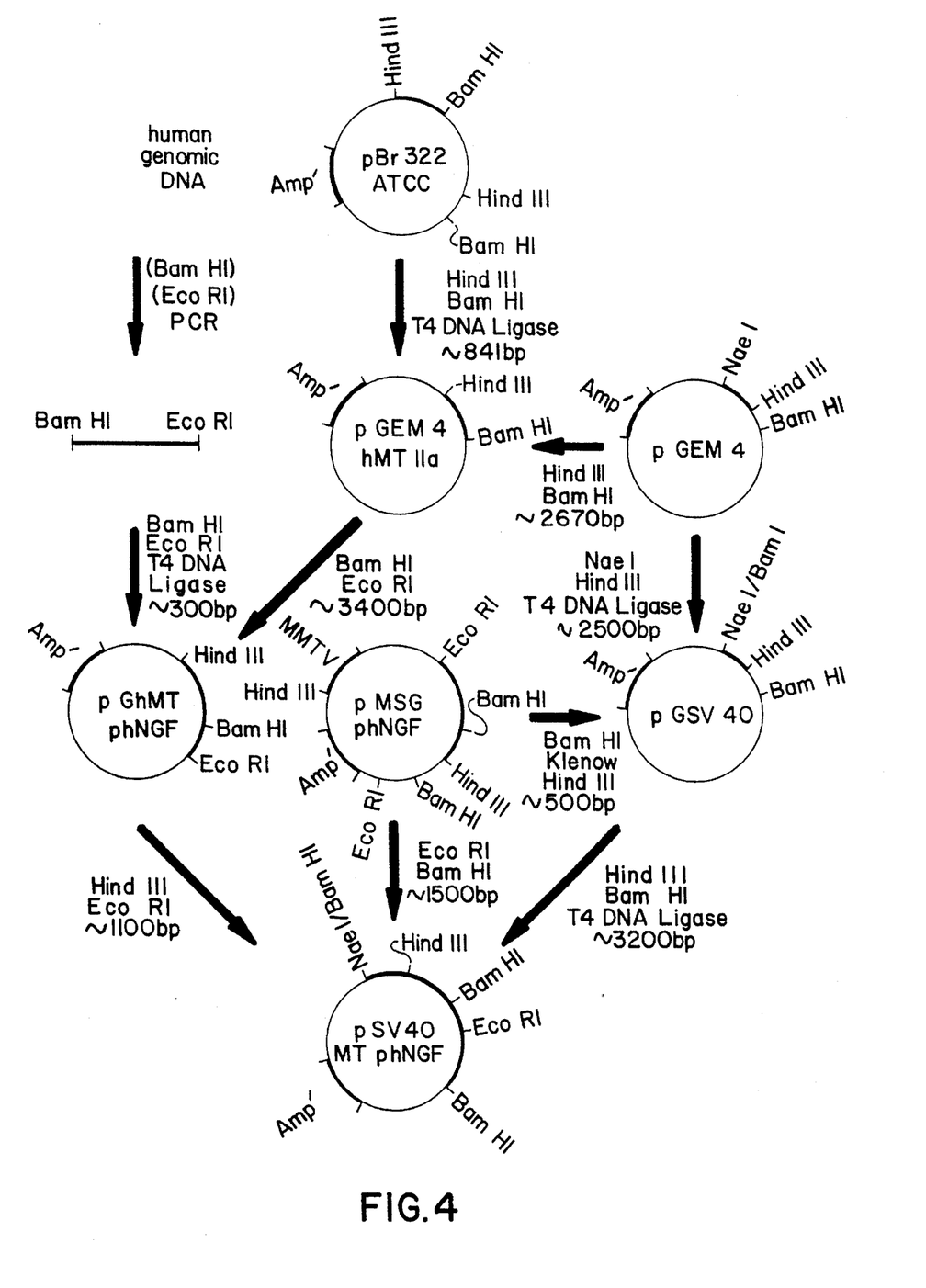
FIG. 4 is a diagrammatic representation of the construction of the pSV40MTphNGF expression vector.
Figure 5:
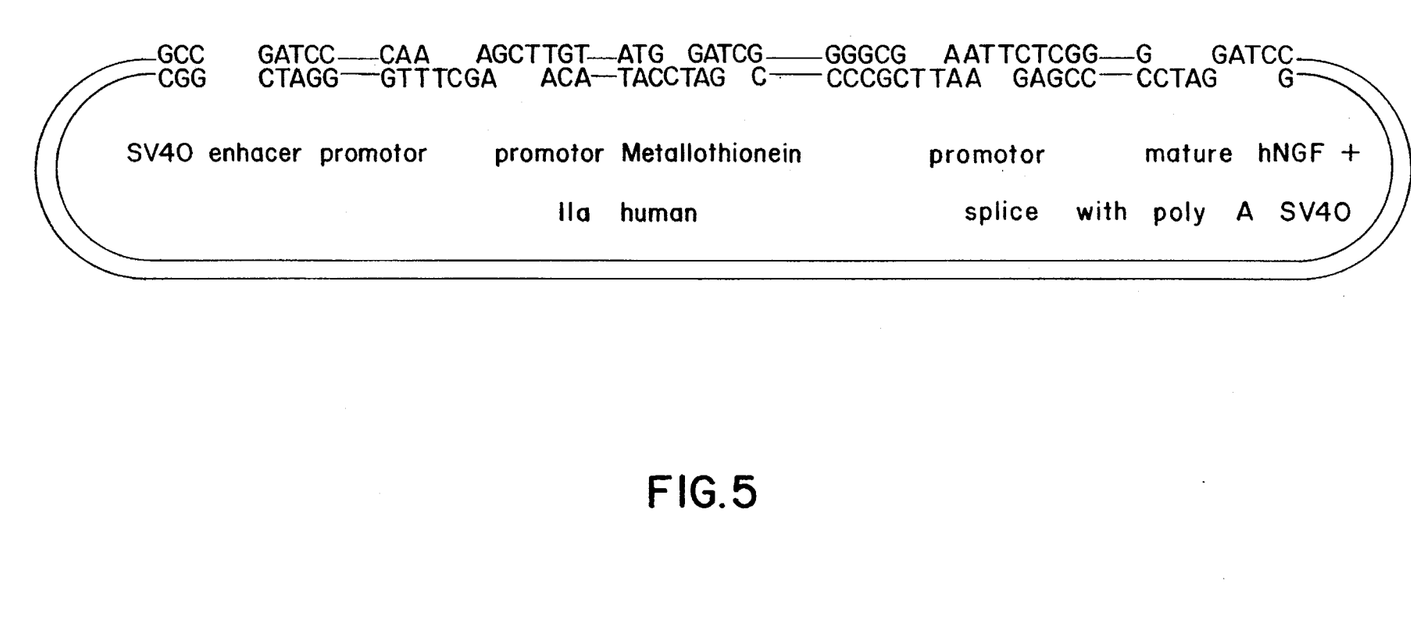
FIG. 5 is a diagrammatic representation of the pSV40MTphNGF expression vector.

To obtain the expression vector the above-mentioned pieces are joined in a triple union of fragments as follows: the pMSGphNGF vector is cut with EcoRI and BamHI restriction enzymes and the fragment of 1500 bp is purified. The pGhHTphNGF vector is cut with the HindIII-EcoRI enzymes and the fragment of 1100 bp is purified. These two fragments are cloned together in pGSV40 vector between HindIII and BamHI restriction sites. The summary diagram for obtaining this expression vector called pSV40MTphNGF is set forth in FIG. 4, while the diagrammatic representation of the same vector is indicated in FIG. 5.

This vector, pSV40MTphNGF, is stably introduced in the CHO KI cells as a double transfection together with the pSV2Neo plasmid and selected as above by neomycin G418 (GIBCO, BRL) 1 mg/ml. This plasmid is cotransfected with the phMT plasmid to obtain selection of colonies containing a high number of copies. In this case, the CHO KI cells are exposed for 24 hours in 50 mN of zinc sulfate to induce the synthesis of metallothionein and selected with cadmium chloride starting with a concentration of 2.5 μM to 20 μM. The cells containing a high number of copies of the hNGF are used for the expression of the molecule.

B.4. cloning of the NGF under the Promoter Enhancer of SV40

Figure 6:
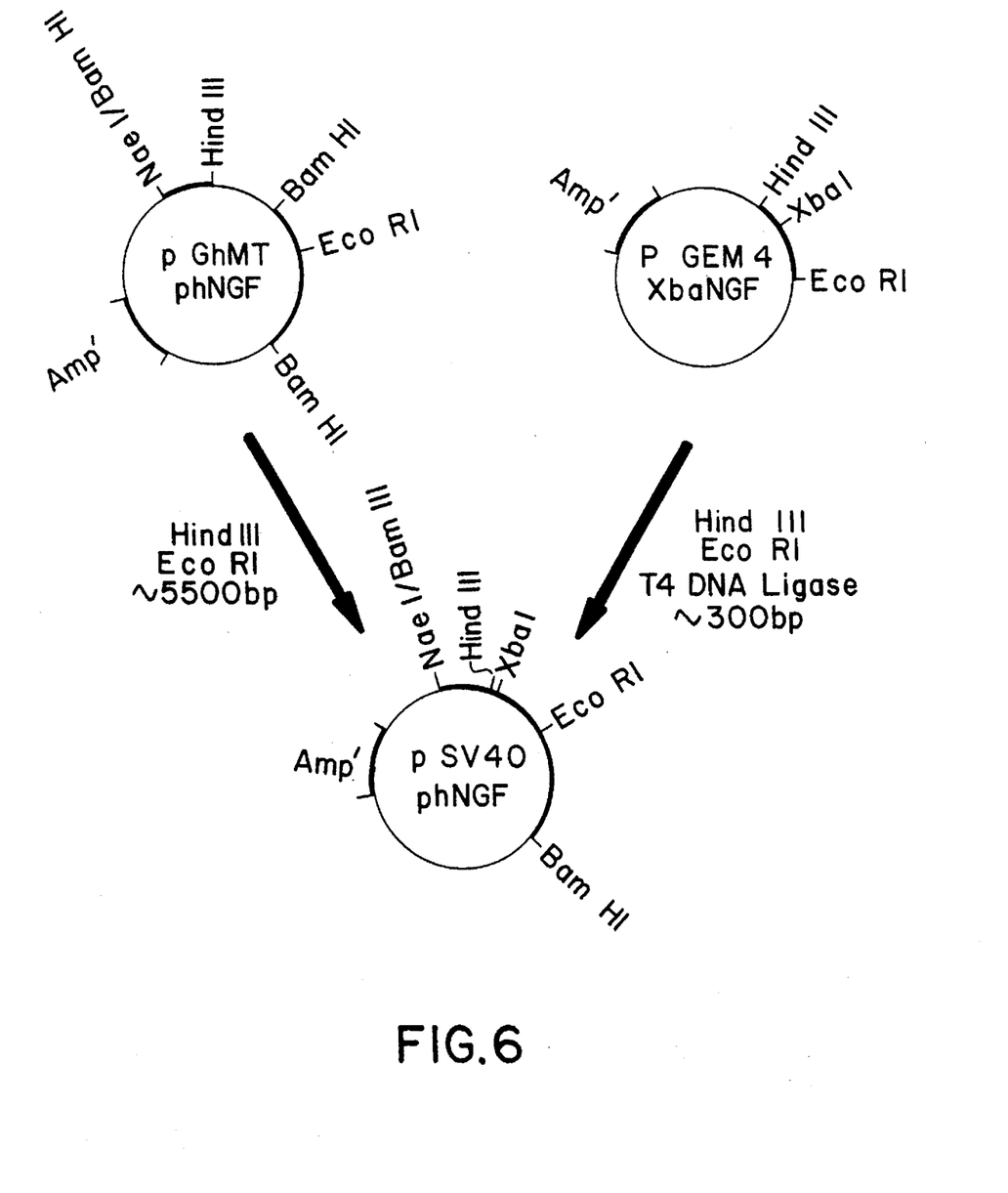
FIG. 6 is a diagrammatic representation of the construction of the pSV40phNF expression vector.
Figure 7:
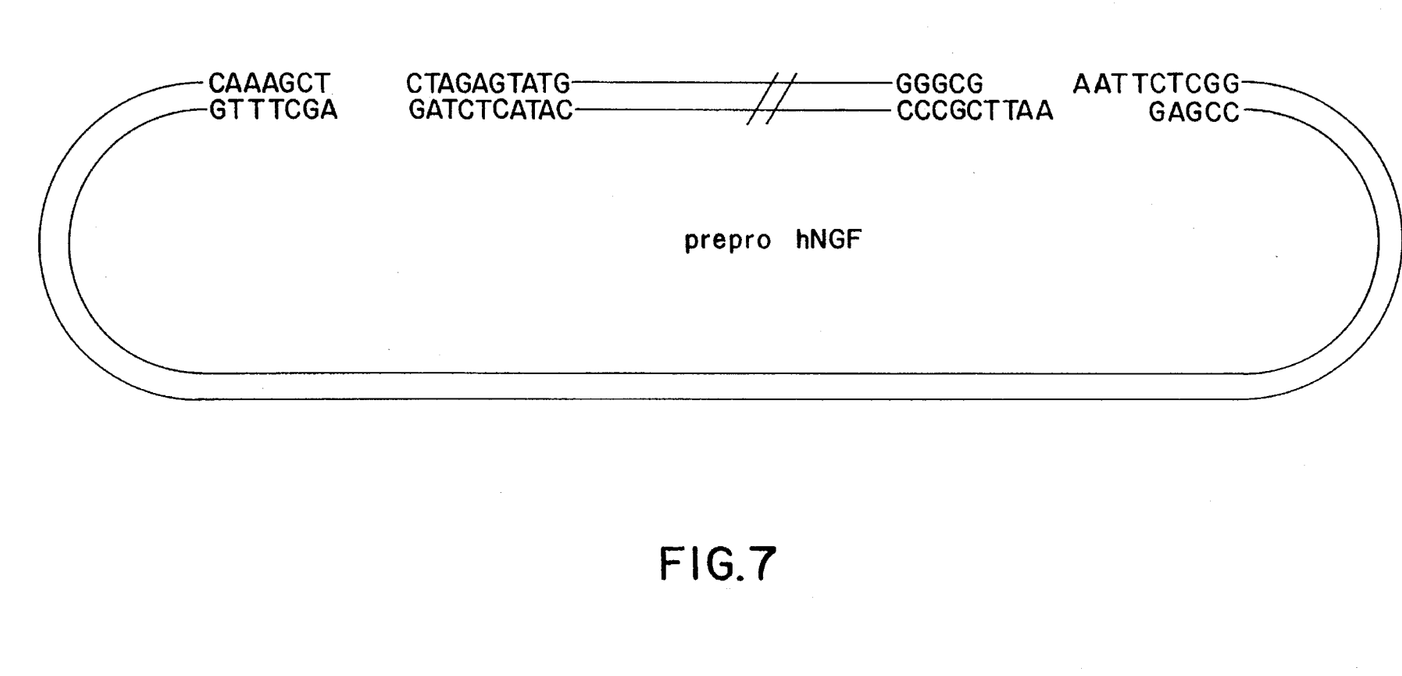
FIG. 7 is a diagrammatic representation of the pSV40phNGF expression vector.

The pGEM4XbaNF plasmid is cut with HindIII and EcoRI restriction enzymes and the fragment of 300 bp is substituted in the pSV40 MT phNGF vector between HindIII and EcoRI restriction sites. The summary diagram for obtaining this vector, called pSV40phNGF, is set forth in FIG. 6, while the diagrammatic representation of the same vector is indicated in FIG. 7.

This is a standard constitutive vector in which the regulatory sequences are assigned to SV40 promoter/enhancer. This vector is stably cotransfected in the CHO KI cells with the pSV2Neo plasmid and the clones producing the β-polypeptide of the nerve growth factor are analyzed.

Selection in the CHO KI dhfr Cells

Figure 8:
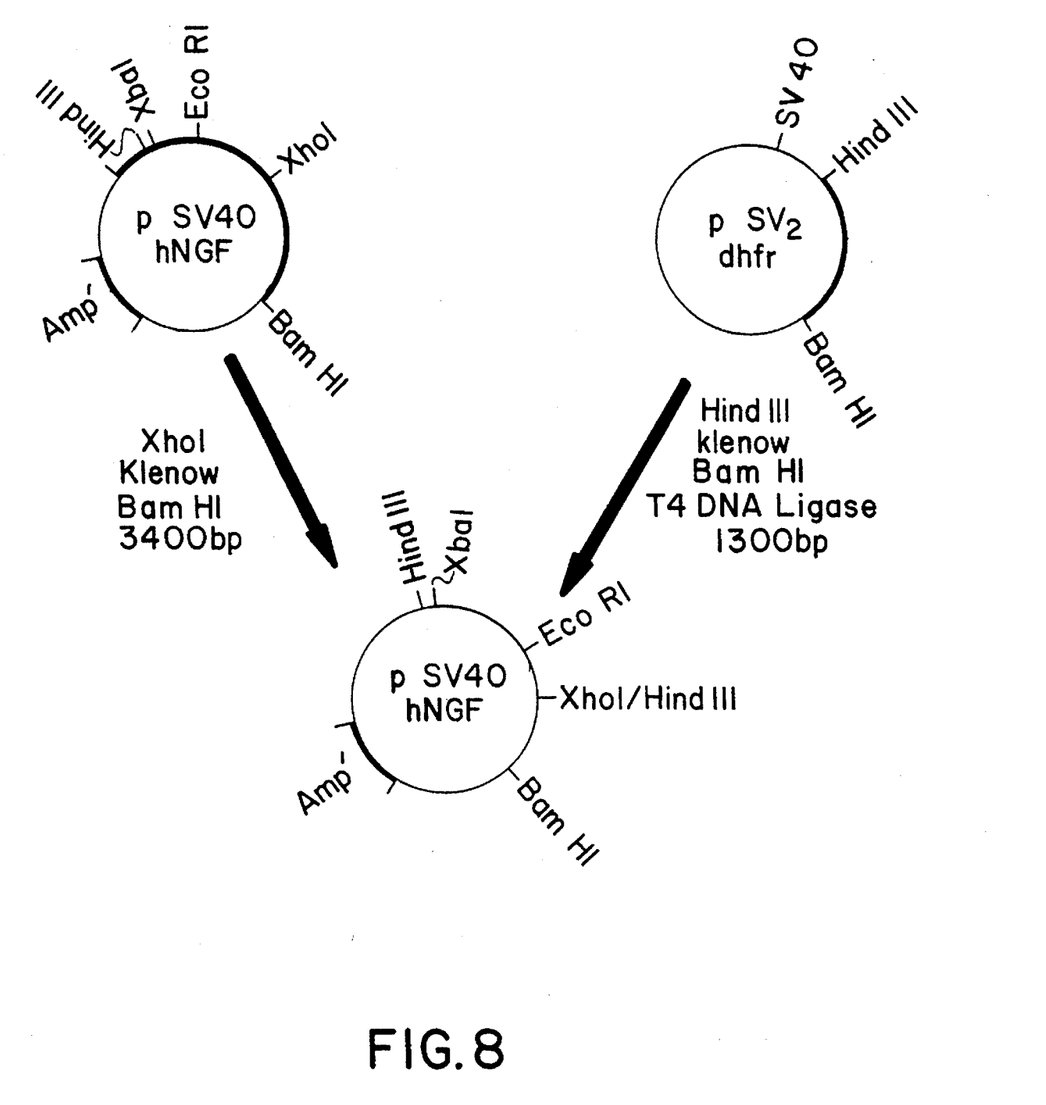
FIG. 8 is a diagrammatic representation of the construction of the pSV40hNGF expression vector.

To obtain the gene amplification of the preceding vector in the CHO KI Dfhr-, the vector is modified subsequently by cloning the gene of DHFR+ upstream from the gene of the hNGF. The pSV2dhfr vector coding for DHFR+ was cut at HindIII and then the extension is copied at 5' with polymerase. Then it is cut at BamH and the fragment of 1800 bp is cloned in the XhoI restriction sites, made blunt with polymerase as above, and BamHI in the pSV40hNGF vector. In this way the pSV40hNGF expression-selection plasmid is created. The summary diagram for obtaining this vector is set forth in FIG. 8.

This plasmid is transfected normally in CHO KI cells in an alpha MEM medium without nucleosides with 10% of cow fetal serum. After two days, the cells are trypsinized and brought to 1/10 of the preceding concentration and the amplification is begun with 10 μM of MTX (methotrexate) up to 500 μM. The cells that survived the highest concentrations of MTX are used for the expression of the hNGF.

Determination of Biological Activity

In vitro studies to determine the biological activity in the culture medium of the CHO cell line after insertion of one of the three vectors described above, after their stabilization, are conducted in chromaffinoma fetal cells PC-12 (Greene L. A. et al., Rev. Neurosci. 3:353, 1982). The specificity of the reaction is checked by using a culture medium where the untransformed CHO lines are growing or by blocking the activity of the hβ-NGF present in the culture medium with polyclonal antibodies specific for the NGF of murine origin or bovine origin. The three cell lines transformed and stabilized with the individual vectors described above produce the β-subunit of the human NGF in biologically active form.

Pharmaceutical compositions

The hβ-NGF of the invention can be formulated according to known methods to produce pharmaceutically useful compositions. The formulation of pharmaceutical compositions containing the human NGF molecule (β-subunit) derived from recombinant DNA, described in this regard without and possibly also with gangliosides and phospholipids, comprises already known methods for the preparation of compositions that are acceptable from the pharmaceutical viewpoint, able to be administered to a patient, which make it possible for an effective amount of the hNGF molecule to be combined in a mixture with a vehicle acceptable from the pharmaceutical viewpoint. Suitable vehicles and their formulation comprising other proteins are described, for example, in "Remington's Pharmaceutical Sciences" (Remington's Pharmaceutical Sciences, Mack Publishing Company, Easton, Pa., USA, 1985). These vehicles comprise injectable "deposit formulations."

On the basis of the above, the pharmaceutical formulation comprises, although not exclusively, solutions of nerve growth factor or its freeze-dried powders in association with one or more vehicles or diluents acceptable from the pharmaceutical viewpoint, and contained in means buffered to suitable pH, and isosmotic with the physiological liquids. In the case of freeze-dried preparations, support excipients can be used, such as, for example but not exclusively, mannitol or glycinin, and suitable buffered solutions of the desired volume will be provided to obtain adequate isotonic buffered solutions having the desired pH. Similar solutions can be used for pharmaceutical solutions for pharmaceutical compositions of the molecule of the nerve growth factor obtained from recombinant DNA in isotonic solutions of the desired volume and include, but not exclusively, the use of physiological buffered solutions with phosphate or citrate in suitable concentrations to obtain each time isotonic pharmaceutical preparations of the desired pH, for example, neutral pH.

The pharmaceutical formulation further comprises, but without being limited to them, suppositories for rectal administration with freeze-dried excipients, for example, water-soluble, autoemulsive of the glycogelatine type or other. In these preparations, the nerve growth factor obtained from the recombinant DNA can be present in amounts varying between 0.01% and 1/1% by weight of the entire excipient. The suppositories can contain, without being limited to them, suitable amounts of acetylsalicylate.

These pharmaceutical preparations can be intended for oral, rectal, parenteral, local, inhalant, intracerebral use. Therefore, they are in solid or semisolid form, for example, dragees, tablets, gelatinous opercula, capsules, suppositories, capsules of soft gelatin. For parenteral and intracerebral use, forms can be used that are intended for intramuscular, subcutaneous administration or suitable for intravenous or intracerebral infusions or injections and therefore can be solutions of active compounds and freeze-dried powders of the active compounds to be joined to one or more recipients or diluents that are acceptable from the pharmaceutical viewpoint, suitable for the above-mentioned uses and of osmolarity compatible with the physiological liquids. For local use, preparations in the form of cream or ointments are considered for topical use; for inhalant use, preparations in spray form, for example nasal sprays, are considered.

The preparations of the invention can be intended for administration to humans or animals. They preferably contain from 0.01% to 10% of the active component for solutions, sprays, ointments and creams and from 1% to 100% and preferably from 5% to 50% of the active compound for preparations in solid form. The dosage to be administered will depend on the indication, on the effect desired and the mode of administration selected.

The invention also comprises the therapeutic use of all the new complexes of gangliosides or derivatives with β-subunit of the nerve growth factor NGF for the indications already mentioned above. The daily dosage for humans by injection (subcutaneous or intramuscular or intracerebral) vary from 0.05 mg to 5 mg of active substance per kg of body weight.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:1:

```
          GCATAGCGTA  ATG  TCC  ATG  TTG  TTC  T                 26
                      Met  Ser  Met  Leu  Phe
                       1                  5
```

( 2 ) INFORMATION FOR SEQ ID NO:2:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:2:

```
          TGT  CTAG  AGT  ATG  TCC  ATG  TTG  TTC  T             26
                    Met  Ser  Met  Leu  Phe
                     1                  5
```

( 2 ) INFORMATION FOR SEQ ID NO:3:

( i ) SEQUENCE CHARACTERISTICS:
        ( A ) LENGTH: 22
        ( B ) TYPE: nucleic acid -continued (C) STRANDEDNESS: single
(D) TOPOLOGY: linear (i i) MOLECULE TYPE: DNA (x i) SEQUENCE DESCRIPTION: SEQ ID NO:3:

GGCGG AATT CTCGGTGGTGGAC          22

(2) INFORMATION FOR SEQ ID NO:4:

(i) SEQUENCE CHARACTERISTICS:
(A) LENGTH: 28
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:4:

```
TG  TCC  ATG  TTG  TTC  TAC  ACT  CTG  ATC  AC          28
    Met  Ser  Met  Leu  Phe  Tyr  Thr  Leu  Ile
    1                   5
```

(2) INFORMATION FOR SEQ ID NO:5:

(i) SEQUENCE CHARACTERISTICS:
(A) LENGTH: 28
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:5:

TGG ATCC ATTGTTCTACACTCTGATCAC          28

(2) INFORMATION FOR SEQ ID NO:6:

(i) SEQUENCE CHARACTERISTICS:
(A) LENGTH: 27
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:6:

TGT CTAG AGAT ATG TCC ATG TTG TTC T          27

(2) INFORMATION FOR SEQ ID NO:7:

(i) SEQUENCE CHARACTERISTICS:
(A) LENGTH: 22
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:7:

GGCGG AATT CTCGGTGGTGGAC          22

The invention being as described, it is clear that these methods can be modified in various ways. Such modifications are not to be considered as deviations from the spirit and perspectives of the invention and all those modifications that will appear evidence to one skilled in the art are comprised within the scope of the following claims:

We claim:

1. A recombinant DNA plasmid which is a plasmid selected from the group consisting of pMSGphNGF as shown in FIGS. 2 and 3 of the specification, pSV40MTphNGF as shown in FIGS. 4 and 5 of the specification and pSV40phNGF as shown in FIGS. 6 and 7 of the specification.

Figure 2:
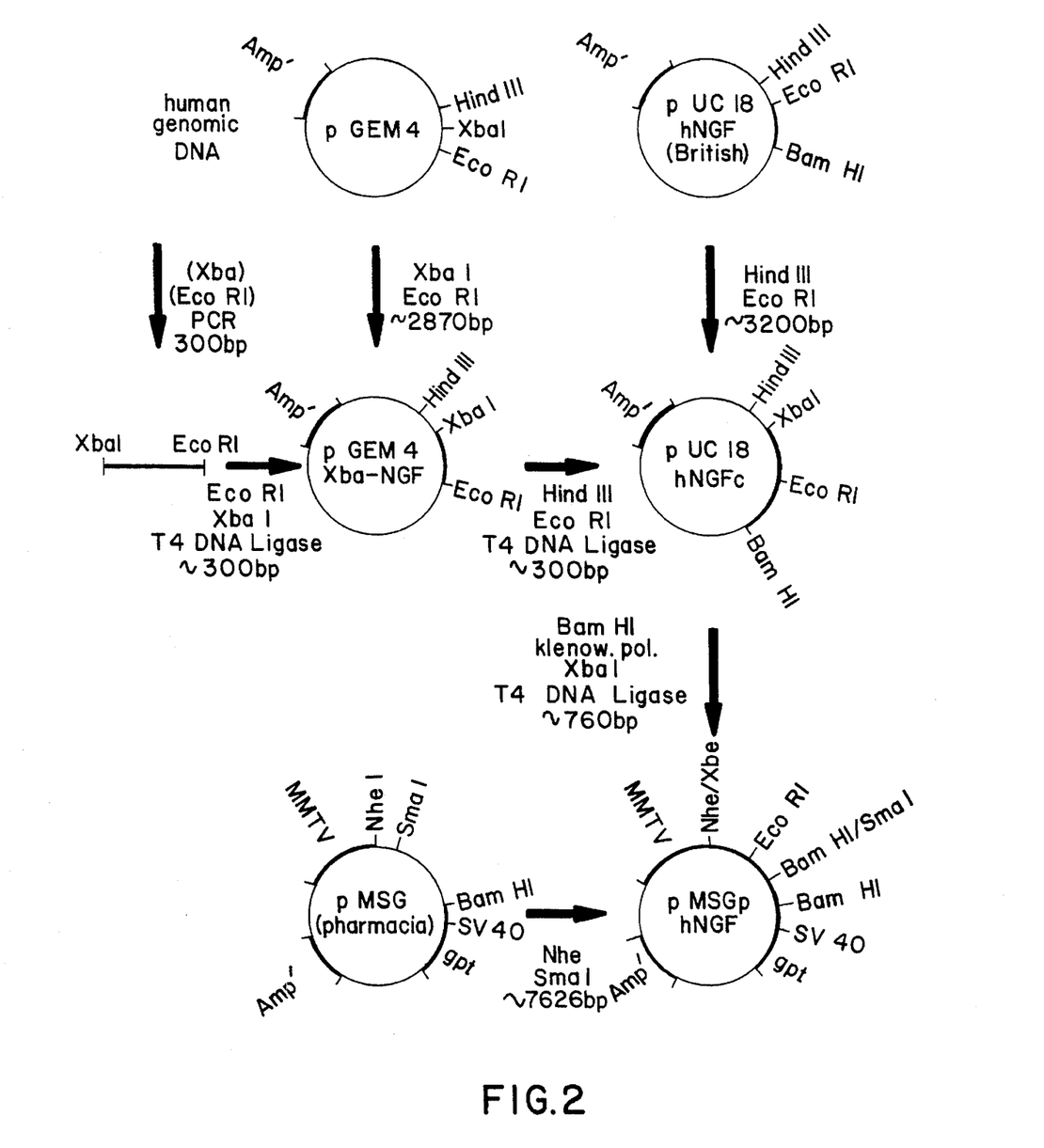
FIG. 2 is a diagrammatic representation of the construction of the pMSGphNGF expression vector.
Figure 3:
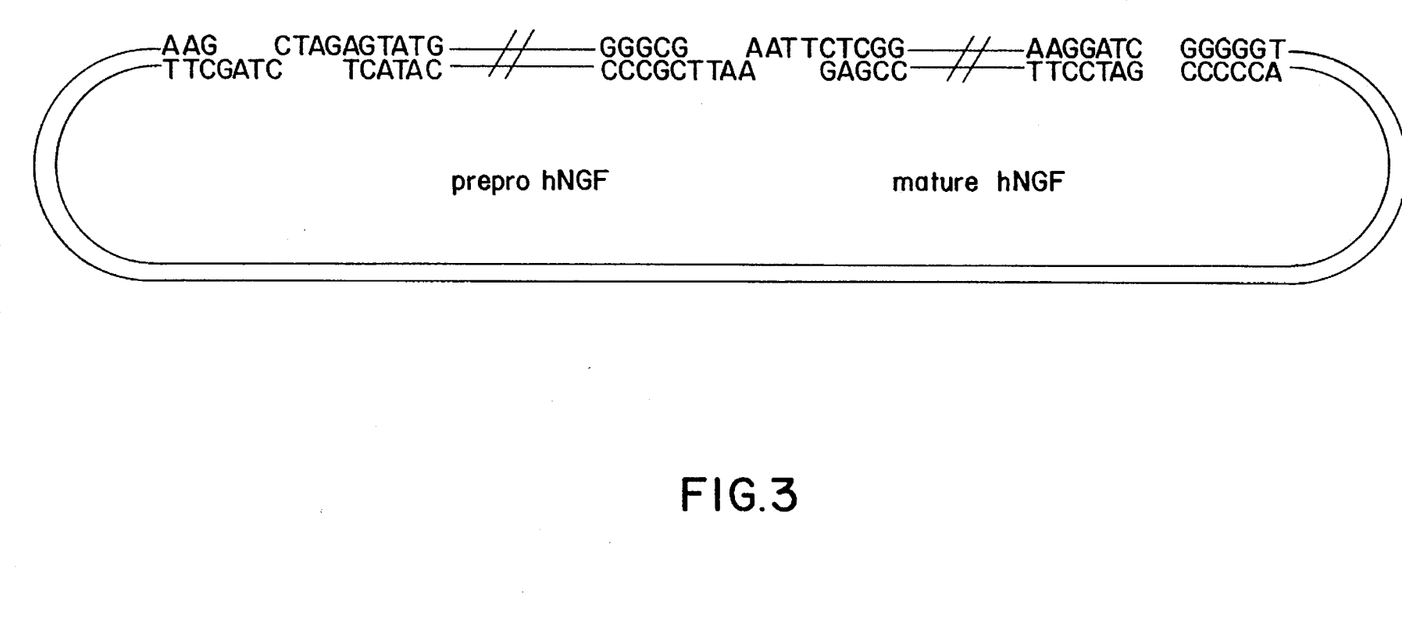
FIG. 3 is a diagrammatic representation of the pMSGphNGF expression vector.

2. A process for the production of human βNGF by culture of a recombinant mammalian cell line, the improvement which comprises:

i) establishing a cell line by tranfecting CHO cells with a plasmid pMSGphNGF, as shown in FIGS. 2 and 3;

ii) culturing said established cell line so as to obtain human βNGF expressed from mRNA which is translated beginning at the methionine encoded by the codon positioned 121 residues upstream from the sequence encoding the pre-pro peptide cleavage site of the human NGF protein.

3. A process for the production of human βNGF by culture of a recombinant mammalian cell line, the improvement which comprises:

i) establishing a cell line by tranfecting CHO cells with a plasmid pSV40MTphNGF, as shown in FIGS. 4 and 5;

ii) culturing said established cell line so as to obtain human βNGF expressed from mRNA which is translated beginning at the methionine encoded by the codon positioned 121 residues upstream from the sequence encoding the pre-pro peptide cleavage site of the human NGF protein.

4. A process for the production of human βNGF by culture of a recombinant mammalian cell line, the improvement which comprises:

i) establishing a cell line by tranfecting CHO cells with a plasmid pSV40phNGF, as shown in FIGS. 6 and 7;

ii) culturing said established cell line so as to obtain human βNGF expressed from mRNA which is translated beginning at the methionine encoded by the codon positioned 121 residues upstream from the sequence encoding the pre-pro peptide cleavage site of the human NGF protein.

* * * * *